US007628779B2

(12) United States Patent
Aneas

(10) Patent No.: US 7,628,779 B2
(45) Date of Patent: Dec. 8, 2009

(54) DEVICE FOR CONNECTION BETWEEN A RECEPTACLE AND A CONTAINER AND READY-TO-USE ASSEMBLY COMPRISING SAME

(75) Inventor: Antoine Aneas, Menetrol (FR)

(73) Assignee: Biodome, Issoire (FR)

( * ) Notice: Subject to any disclaimer, the term of this patent is extended or adjusted under 35 U.S.C. 154(b) by 841 days.

(21) Appl. No.: 10/504,837

(22) PCT Filed: Feb. 19, 2003

(86) PCT No.: PCT/FR03/00555

§ 371 (c)(1),
(2), (4) Date: Nov. 25, 2005

(87) PCT Pub. No.: WO03/070147

PCT Pub. Date: Aug. 28, 2003

(65) Prior Publication Data

US 2006/0287638 A1 Dec. 21, 2006

(30) Foreign Application Priority Data

Feb. 20, 2002 (FR) .................................. 02 02149

(51) Int. Cl.
*A61B 19/00* (2006.01)

(52) U.S. Cl. ...................... 604/411; 604/414; 604/415; 604/416

(58) Field of Classification Search ................. 604/403, 604/411, 414, 415, 416; 206/363–366
See application file for complete search history.

(56) References Cited

U.S. PATENT DOCUMENTS 2,847,996 A 8/1958 Cohen et al.

(Continued)

FOREIGN PATENT DOCUMENTS

DE 41 22 476 A1 1/1993

(Continued)

OTHER PUBLICATIONS

PCT International Preliminary Examination Report, International Application No. PCT/FR2003/000555, International Filing Date Feb. 19, 2003, Priority Date Feb. 20, 2002.

*Primary Examiner*—Leslie R Deak
(74) *Attorney, Agent, or Firm*—K&L Gates LLP

(57) ABSTRACT

The invention concerns a connection device comprising a base (10) adapted to be mounted on a receptacle (2) and forming a sliding sleeve (15) for a piston (16) which moves or forms a hollow needle (16), an annular skirt (20) for locking the base plate (10) in snap-on configuration on the neck (4), and a cap (30) designed to isolate the plate (10) and/or the piston (16) from ambient atmosphere. The cap (30) is provided with at least one protuberance (33) designed to be engaged in the internal volume (V) of said skirt (20), said protuberance (33) extending radially relatively to a central axis (X-X') of the cap (30) over a distance ($R_{33}$) greater than the minimum distance ($R_{25}$) between said central axis (X-X') and an edge (23) of the opening (O') providing access to the internal volume (V) of said skirt. The protuberance remains integral with the rest (31*a*) of the cap when the latter is removed from the device. Once the cap (30) is removed from the skirt (20), the protuberance counters its re-insertion into the internal volume (V) of the skirt.

20 Claims, 9 Drawing Sheets

U.S. PATENT DOCUMENTS

| | | | | | |
|---|---|---|---|---|---|
| 3,902,491 | A | | 9/1975 | Lajus | |
| 3,976,073 | A | | 8/1976 | Quick et al. | |
| 4,116,196 | A | | 9/1978 | Kaplan et al. | |
| 4,195,632 | A | | 4/1980 | Parker et al. | |
| 4,296,786 | A | | 10/1981 | Brignola | |
| 4,507,113 | A | | 3/1985 | Dunlap | |
| 4,552,277 | A | | 11/1985 | Richardson et al. | |
| 4,576,211 | A | | 3/1986 | Valentini et al. | |
| 4,589,879 | A | | 5/1986 | Pearson | |
| 4,607,671 | A | | 8/1986 | Aalto et al. | |
| 4,639,250 | A | | 1/1987 | Rycroft | |
| 4,675,020 | A | | 6/1987 | McPhee | |
| 4,713,060 | A | | 12/1987 | Riuli | |
| 4,759,756 | A | | 7/1988 | Forman et al. | |
| 4,883,483 | A | | 11/1989 | Lindmayer | |
| 4,898,209 | A | | 2/1990 | Zbed | |
| 5,060,704 | A | | 10/1991 | Rohrbough | |
| 5,152,965 | A | | 10/1992 | Fisk et al. | |
| 5,169,388 | A | | 12/1992 | McPhee | |
| 5,186,323 | A | | 2/1993 | Pfleger | |
| 5,224,515 | A | | 7/1993 | Foster et al. | |
| 5,232,029 | A | | 8/1993 | Knox et al. | |
| 5,247,972 | A | | 9/1993 | Tetrault | |
| 5,279,576 | A | | 1/1994 | Loo et al. | |
| 5,279,583 | A | | 1/1994 | Shober, Jr. et al. | |
| 5,300,040 | A | | 4/1994 | Martin | |
| 5,308,347 | A | | 5/1994 | Sunago et al. | |
| 5,336,180 | A | | 8/1994 | Kriesel et al. | |
| 5,342,346 | A | | 8/1994 | Honda et al. | |
| 5,342,347 | A | | 8/1994 | Kikuchi et al. | |
| 5,350,372 | A | | 9/1994 | Ikeda et al. | |
| 5,352,191 | A | | 10/1994 | Sunago et al. | |
| 5,364,386 | A | | 11/1994 | Fukuoka et al. | |
| 5,374,264 | A | | 12/1994 | Wadsworth, Jr. | |
| 5,397,303 | A | | 3/1995 | Sancoff et al. | |
| 5,423,753 | A | | 6/1995 | Fowles et al. | |
| 5,423,791 | A | | 6/1995 | Bartlett | |
| 5,429,256 | A | | 7/1995 | Kestenbaum | |
| 5,429,614 | A | | 7/1995 | Fowles et al. | |
| 5,478,337 | A | | 12/1995 | Okamoto et al. | |
| 5,526,853 | A | | 6/1996 | McPhee et al. | |
| 5,569,206 | A | * | 10/1996 | Gorman et al. | 604/167.01 |
| 5,636,660 | A | | 6/1997 | Pfleiderer et al. | |
| 5,653,686 | A | | 8/1997 | Coulter et al. | |
| 5,697,915 | A | | 12/1997 | Lynn | |
| 5,701,910 | A | | 12/1997 | Powles et al. | |
| 5,772,652 | A | | 6/1998 | Zielinski | |
| 5,807,323 | A | | 9/1998 | Kriesel et al. | |
| 5,873,872 | A | | 2/1999 | Thibault et al. | |
| 5,879,345 | A | | 3/1999 | Aneas | |
| 5,925,029 | A | | 7/1999 | Jansen et al. | |
| 6,022,339 | A | | 2/2000 | Fowles et al. | |
| 6,063,068 | A | | 5/2000 | Fowles et al. | |
| 6,070,623 | A | | 6/2000 | Aneas | |
| 6,213,994 | B1 | | 4/2001 | Jansen et al. | |
| 6,280,430 | B1 | | 8/2001 | Neftel et al. | |
| 6,280,431 | B1 | * | 8/2001 | Domkowski et al. | 604/411 |
| 6,299,608 | B1 | | 10/2001 | Solomon et al. | |
| 6,382,442 | B1 | * | 5/2002 | Thibault et al. | 215/249 |
| 6,478,788 | B1 | | 11/2002 | Aneas | |
| 6,537,263 | B1 | | 3/2003 | Aneas | |
| 6,681,946 | B1 | * | 1/2004 | Jansen et al. | 215/249 |
| 6,695,829 | B2 | | 2/2004 | Hellstrom et al. | |
| 6,746,438 | B1 | | 6/2004 | Arnissolle | |

FOREIGN PATENT DOCUMENTS

| | | | | |
|---|---|---|---|---|
| DE | 295 16 650 | U1 | | 2/1996 |
| EP | 0 458 543 | A1 | | 11/1991 |
| EP | 0 538 891 | A1 | | 4/1993 |
| EP | 0 737 485 | A1 | | 10/1996 |
| EP | 0 728 457 | A2 | | 11/1996 |
| EP | 0 728 457 | A3 | | 11/1996 |
| EP | 0 829 250 | A2 | | 3/1998 |
| EP | 0 829 250 | A3 | | 3/1998 |
| EP | 0 728 457 | B1 | | 1/1999 |
| FR | 1423549 | | | 2/1965 |
| FR | 2753624 | A1 | | 3/1998 |
| WO | WO 90/03536 | A1 | | 4/1990 |
| WO | WO 96/00053 | A1 | | 1/1996 |
| WO | WO 97/10156 | A1 | | 3/1997 |
| WO | WO 98/13006 | A1 | | 4/1998 |
| WO | WO 99/27886 | A1 | | 6/1999 |
| WO | WO 99/53886 | A1 | | 10/1999 |
| WO | WO 00/24442 | A1 | | 5/2000 |
| WO | WO 00/47159 | A1 | | 8/2000 |
| WO | WO 01/32524 | | * | 5/2001 |

* cited by examiner

DEVICE FOR CONNECTION BETWEEN A RECEPTACLE AND A CONTAINER AND READY-TO-USE ASSEMBLY COMPRISING SAME

This Application is a U.S. National filing under §371 of International Application No. PCT/FR03/00555, filed 19 Feb. 2003, claiming priority from French Appln. No. 02/02149, filed 20 Feb. 2002, now pending (which is hereby incorporated by reference).

The invention relates to a device for connection between a closed receptacle and a container. The invention also relates to a ready-to-use assembly comprising, inter alia, a closed receptacle and a connection device of the afore-mentioned type.

In the domain of packaging of medicines, it is known to store a component of a pharmaceutical preparation, such as, for example, its active ingredient, in a receptacle closed by a stopper of relatively non-rigid material, for example made of elastomer. A liquid may be introduced in this receptacle after perforation of the stopper, in order to dissolve or place the component contained in the receptacle in suspension, for the purpose of obtaining a preparation, particularly a medicine or a vaccine., in liquid form and ready to be administered to the patient.

WO-A-97/10156 discloses a connection device which comprises a base adapted to cover the neck of a receptacle and extending in a flange or sleeve forming an inner bore, while a plunger is mounted to slide in this bore. The plunger bears a needle provided to traverse the stopper of the receptacle in a so-called transfer position. This device also comprises a cap allowing the base and the plunger to be isolated with respect to the ambient atmosphere before the plunger is pushed in the direction of the stopper.

After manoeuvring the connection device, and in particular after injection of a liquid and/or withdrawal of part of the preparation that it contains, the cap of this known device may be returned into position thereon, with the result that it is not immediately apparent that the connection device has already been activated and brought into contact with the ambient atmosphere. This might lead to errors in manipulation, particularly by nursing staff who have to work under sometimes considerably stressful conditions.

It is a more particular object of the present invention to overcome these drawbacks by proposing a novel connection device which allows efficient isolation of the plunger and base with respect to the ambient atmosphere and an immediate detection of the fact that such isolation has been broken, this making it easier to differentiate a ready-to-use assembly which has already been activated from a ready-to-use assembly not yet activated.

In that spirit, the invention relates to a device for connection between a closed receptacle and a container, this closed receptacle comprising a neck of which the opening is closed by a stopper, while this connection device comprises:

- a base adapted to be mounted on the receptacle, comprising a sleeve forming an inner bore and adapted to be snapped on the neck;
- a plunger adapted to slide in this bore between a first position, disengaged with respect to the stopper and a second, so-called transfer position, in which a hollow needle displaced or formed by the plunger traverses this stopper;
- an annular skirt for locking the base in snap-on configuration on the neck, and
- a cap adapted to isolate this sleeve and/or this plunger from the ambient atmosphere, and to be withdrawn in order to allow connection of the container, while the cap is provided with at least one protuberance adapted to be engaged in the internal volume of the skirt, this protuberance extending radially with respect to a central axis of the neck and of the cap over a distance greater than the minimum distance between this axis and an edge of an opening providing access to the internal volume of the skirt, while the protuberance is connected to the principal part of the cap.

This device is characterized in that the protuberance of the cap is a radial flange extending on the periphery of the cap, with a radius greater than the internal radius of the edge of the opening of the skirt which is substantially circular and in that the skirt is elastically deformable and compatible with the extraction of the protuberance with respect to its internal volume thanks to an essentially radial deformation of its edge, with the result that it remains integral with the afore-mentioned principal part of the cap when the cap is removed from the device, before it is first used.

Thanks to the invention, the cap remains captive of the skirt inside which it is locked by its protuberance which comes into abutment and is blocked against the edge of the opening. In this first position, the connection device has not yet been used. In order to use the connection device, the cap must be separated from the cover, which involves extracting the protuberance from the internal volume of the skirt. This operation is irreversible, with the result that the user will immediately notice when such an extraction has taken place.

According to advantageous but non-compulsory aspects of the invention, the device incorporates one or more of the following characteristics:

- The geometry of the protuberance of the cap and the geometry of the edge of the opening of the skirt allow the extraction of the protuberance with respect to the internal volume of the skirt, through the afore-mentioned opening and in a direction parallel to the axis of slide of the plunger, while these geometries oppose an introduction of the cap in the afore-mentioned volume through the afore-mentioned opening. In other words, the geometry of the protuberance and of the edge makes it possible to extract the cap from the internal volume of the skirt but opposes a later introduction of the cap in the skirt, this avoiding a fresh positioning of the cap on the base and around the plunger after activation of the device, i.e. after displacement of the plunger from its disengaged position towards its transfer position.
- The flange presents an outer radial surface which is truncated and convergent in the direction of the bottom of the cap, while the edge of the opening of the skirt is truncated and convergent opposite means for snapping the device on the neck. Thanks to this aspect of the invention, the flange and the edge form two truncated surfaces capable of coming into surface abutment against each other, which allows an efficient transmission of effort when the protuberance abuts against the edge of the opening, this effort making it possible to retain the cap in position partially engaged in the skirt. The afore-mentioned transmission of effort also makes it possible to envisage a radial expansion of the edge of the opening under the effect of an effort transmitted by the flange while the cap is being withdrawn.
- An O-ring made of elastomer is provided, interposed between the cap and the base when the afore-mentioned protuberance is engaged in the internal volume of the skirt. This elastomeric O-ring guarantees seal of the cap with respect to the base, including when the connection device is subjected to a terminal sterilization in an autoclave for a duration of about 20 minutes and at a temperature of about 120° C. In that case, the O-ring is advantageously made of injectable elastomer, for example Santoprene (Registered Trademark), such a material conserving the essential of its properties of elasticity after a terminal sterilization treatment. Such is not the case of the plastics material conventionally used for making a base or a cap, such as polypropylene or polyethylene, while compounds based on styrene are likely to melt at the sterilization temperatures employed.

The cap is provided with a tapping adapted to cooperate with at least one protuberance formed on the outer surface of the sleeve for positioning the cap along the axis of slide of the plunger. Such tapping and protuberance make it possible to considerably increase the effort exerted by a user on the cap and transmitted to the edge of the opening, which makes it possible to exert a sufficient effort of radial expansion of this edge. This protuberance and tapping also make it possible to exert an effort of compression of the injectable elastomer O-ring when such a seal is provided.

The cap and the skirt are in one-piece, and made in the form of a single piece of plastics material, breakable bridges being provided in order to join this cap and this skirt. The fact of making the cap and the skirt in one piece guarantees their relative positioning at the beginning of assembly and facilitates assembling of the device.

The invention also relates to a ready-to-use assembly which comprises a closed receptacle containing a product, particularly a pharmaceutical preparation, this receptacle being provided with a neck whose opening is closed by a stopper, and a connection device as described hereinbefore mounted on this receptacle. Such a receptacle makes it possible to keep sterile a component of a medicine or a vaccine, particularly its active ingredient, while a user can immediately notice whether such an assembly has already been activated or not.

The invention will be more readily understood and other advantages thereof will be more clearly apparent on reading the following description of two forms of embodiment of a connection device in accordance with its principle, given by way of non-limiting example and made with reference to the accompanying drawings, in which.

Figure 1:
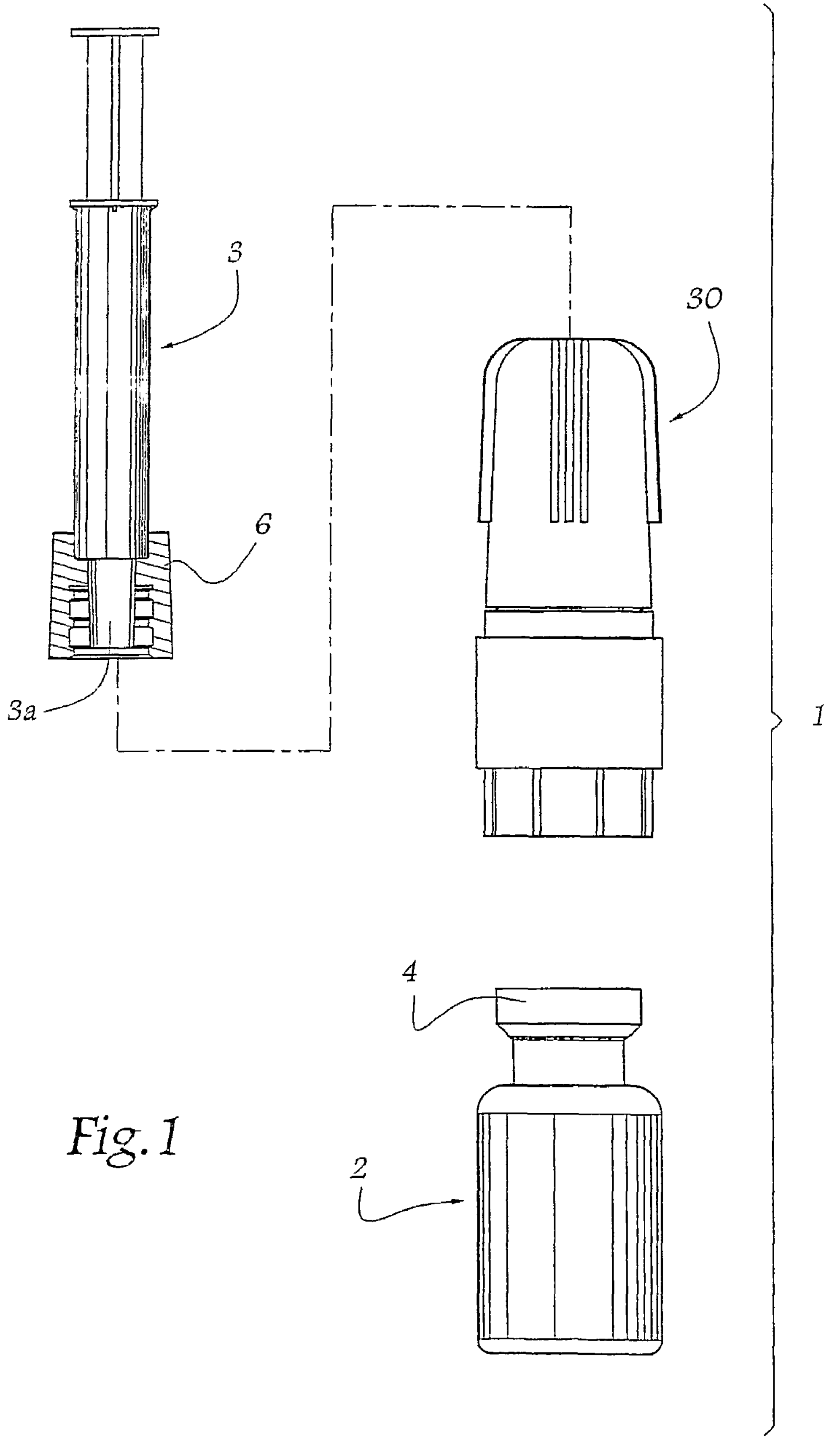
FIG. 1 is an exploded side view of a ready-to-use assembly according to the invention and of a syringe provided to cooperate with this assembly.

The device 1 according to the invention has a dual function. On the one hand, it renders tamperproof a receptacle 2, for example a previously closed or stoppered glass flask, containing a product (not shown). This product may be a powder containing an active ingredient of a medicine or a vaccine. On the other hand, the device 1 ensures or establishes a tight connection between the interior of the receptacle 2 and the interior of another container, such as a syringe 3 containing a liquid intended to place the product contained in the receptacle 2 in solution or in suspension. In place of a syringe, the container might be formed by a supple bag or another glass flask.

The flask 2 comprises a neck 4 of which the opening **4*a* is hermetically closed by a stopper 5 made of a relatively non-rigid material, for example of elastomer, preferably rubber. According to a variant of the invention (not shown), a capsule may be disposed around the stopper 5 and an outer annular part 4*b* of the neck 4**.

The device 1 comprises a base 10 made by injection of polyethylene and/or of polypropylene, which comprises a cylindrical part 11 provided to be centred on the axis of symmetry X-X' of the elements 2, 4 and 5. The part 11 extends in a plurality of elastic tabs 12 each equipped with a spout 13 and adapted to cooperate with the outer surface of the neck 4 with a view to the base 10 being elastically snapped on the neck.

Opposite a lower edge **11*a* intended to penetrate superficially in the upper surface of the stopper 5, the part 11 extends in an annular band 14 for join with a sleeve 15 which forms an inner bore A for storage and displacement of a plunger 16 principally constituted by a hollow needle. The inner radial surface 17 of the sleeve 15** is cylindrical with circular base and centred on axis X-X' which is thus the central axis of the bore A.

Figure 5:
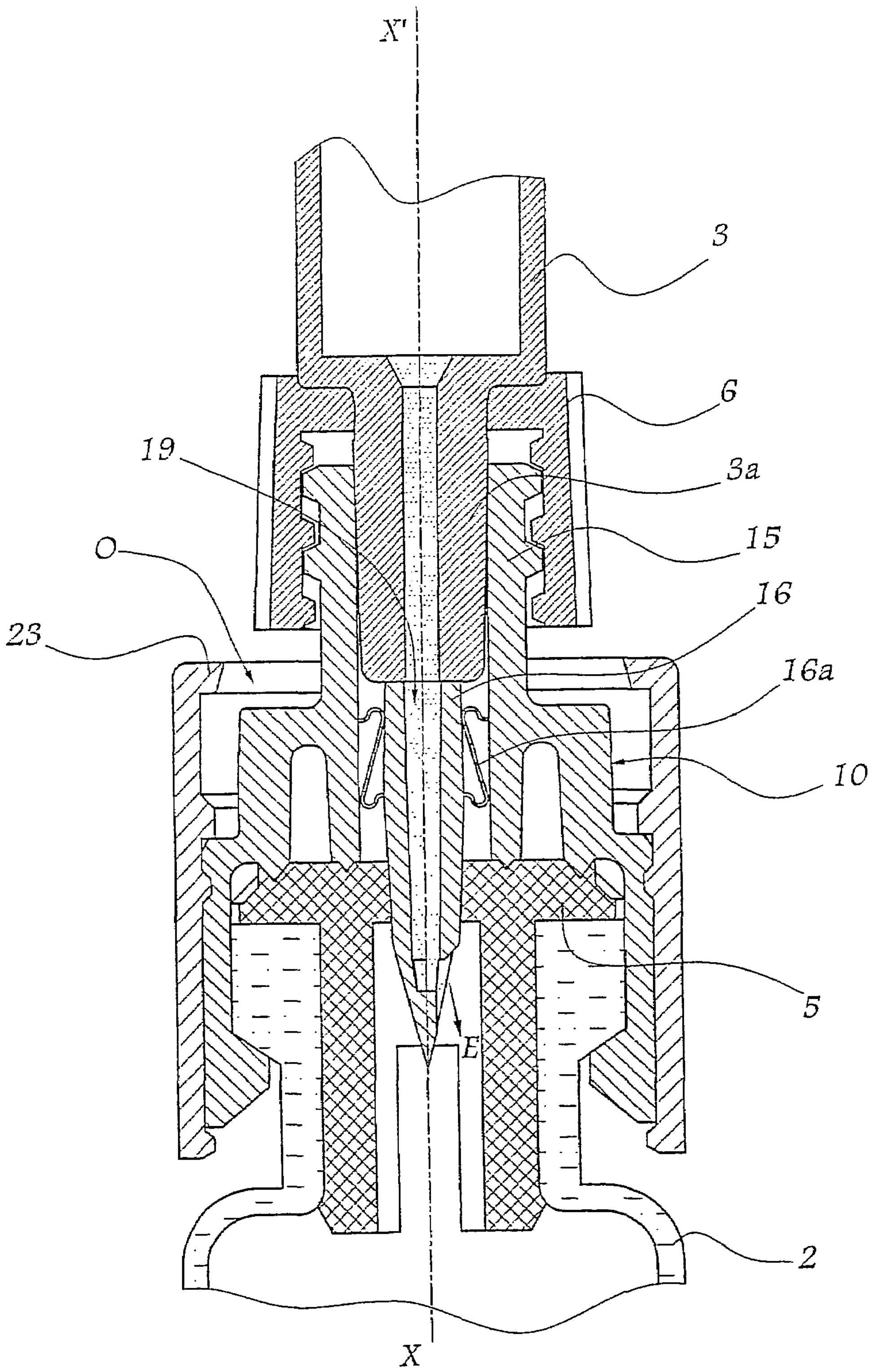
FIG. 5 is a section similar to FIG. 2, when the device is used for transferring a liquid from the syringe towards the receptacle or vice versa.

The sleeve 15 also bears four "ears" $\mathbf{18}_1$, $\mathbf{18}_2$, $\mathbf{18}_3$ and $\mathbf{18}_4$ allowing it to cooperate with a nut 6 associated with the syringe 3. A connecting piece **3*a* of the "LUER LOCK" type is provided on the syringe and is intended to be introduced in the sleeve 15, as shown in FIG. 5**.

The lower edge **15*a* of the sleeve 15 is intended to penetrate superficially in the stopper 5**.

The hollow needle 16 forms a central channel 19 and is joined to the sleeve 15 by three elastic tongues of which two are shown in the Figures under reference **16*a*, with the result that elements 11 to 19** form a single piece, in accordance with the technical teaching of WO-A-01/32524.

Other forms of plunger may be envisaged with the present invention, in particular such as disclosed by WO-A-97/10156, WO-A-98/13006, WO-A-00/16730 or WO-A-00/47159.

A skirt or ring 20 is mounted around the base 10 and comprises two inner beads 21 and 22 intended to be selectively engaged in an outer radial groove **10*a* of the base 10. The passage of the ring 20 from the position of FIG. 2 to that of FIGS. 3 to 6 makes it possible to immobilize the tabs 12 in position around the neck 4**, in accordance with the technical teaching of WO-A-97/10156.

The skirt 20 is provided, opposite the bead 21, with an inner radial flange 23 which forms the edge of an opening O providing access to the internal volume V of the skirt 20, when the latter is in place around the base 10. The inner radial face **23*a* of the flange 23 is truncated, centred on axis X-X' and convergent opposite the bead 21**.

Figure 2:
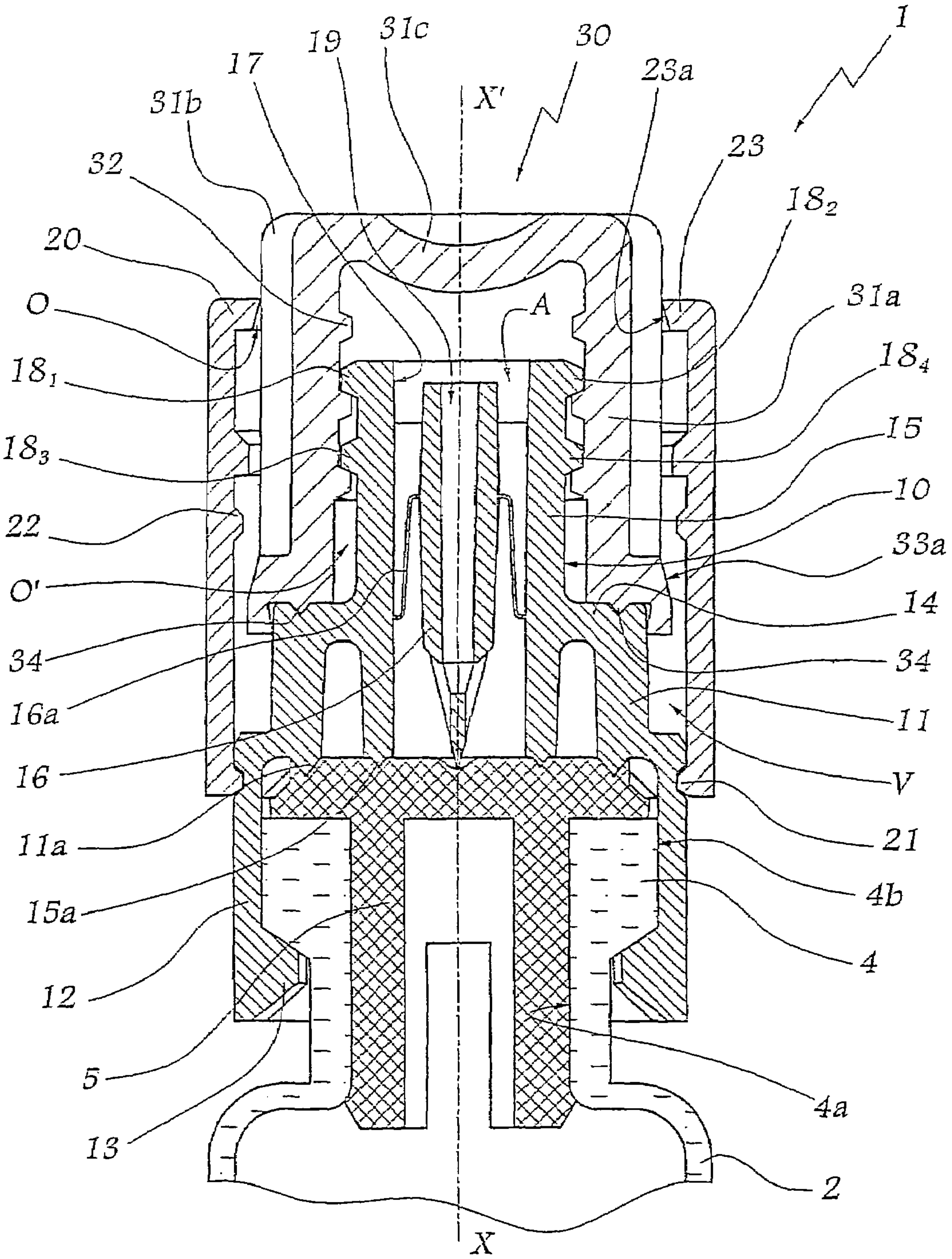
FIG. 2 is an axial section through the connection device of the assembly of FIG. 1 upon positioning of this device on the receptacle of this assembly.
Figure 3:
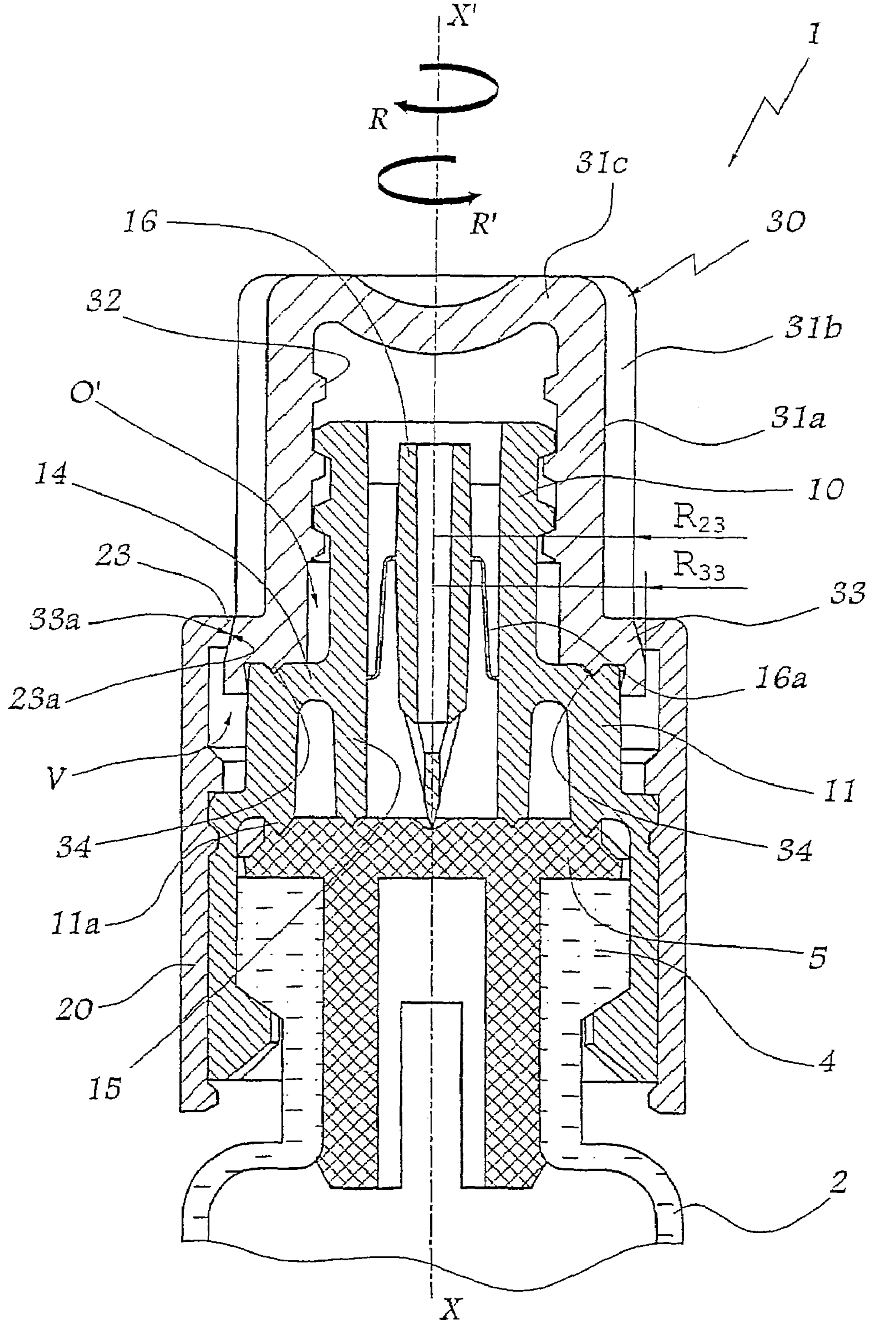
FIG. 3 is a section similar to FIG. 2 when the device is in configuration of storage of the assembly of FIG. 1.
Figure 4:
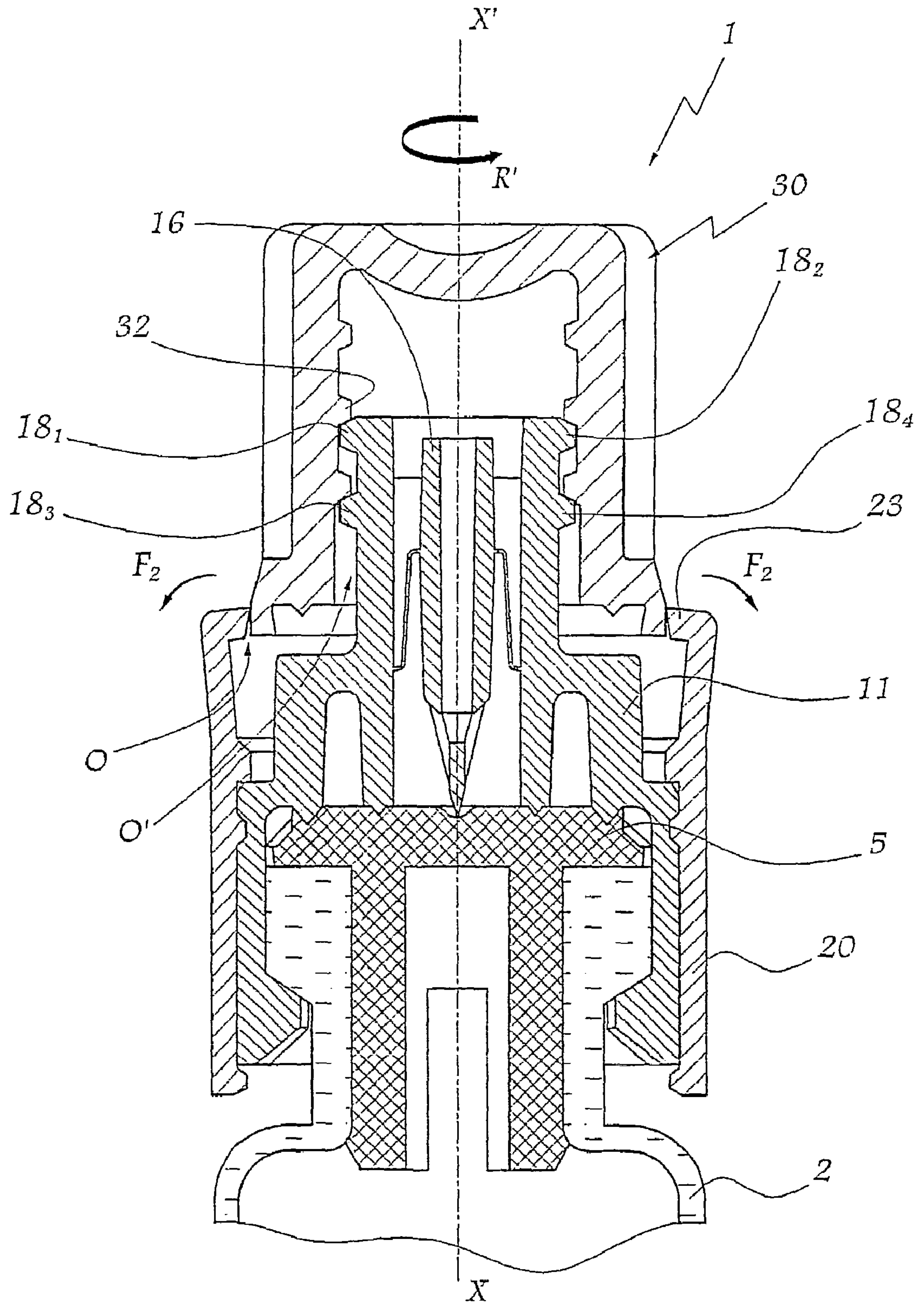
FIG. 4 is a section similar to FIG. 2 upon withdrawal of the cap from the connection device.

A cap 30 is provided around the sleeve 15 and is, in essence, in position in the volume V in the configuration of FIG. 2 while it is, in essence, disposed outside this volume when the ring 20 is in the position of FIGS. 3 to 5.

This cap 30 comprises a principal part **31*a* in the form of a cover substantially symmetrical about the axis X-X' and provided with outer ribs 31*b* facilitating grip in the hand. The cap also comprises a bottom 31*c*. The cap 30 defines an opening O' through which the sleeve 15 can be introduced in this cap. An inner thread 32 forms a tapping inside the cap 30**.

An outer flange 33 in one piece with the cap 30 is adjacent the opening O'. The flange 33 comprises a radial surface 33*a* centered on the axis of symmetry of the cap 30, which merges with the axis X-X', and convergent in the direction of the bottom 31*c*.

The maximum radius $R_{33}$ of the surface 33*a* is greater than the minimum radius $R_{23}$ of the surface 23*a*.

In this way, when the skirt 20 is in the position of FIG. 3, the flange 23 opposes extraction of the flange 33 with respect to the internal volume V of the skirt 20.

More precisely, the respective apex angles $\alpha_{23}$ and $\alpha_{33}$ of the surfaces 23*a* and 33*a* are substantially equal, with the result that a surface abutment of the surfaces 23*a* and 33*a* may be obtained in the configuration of FIG. 3.

Taking the foregoing into account, the flange 23 contributes to holding the cap 30 in position in the configuration of FIG. 3.

The cap 30 also presents teeth 34 provided to penetrate superficially in the band 14, this making it possible to create a tight connection between the cap 30 and the base 10 and to isolate the sleeve 15 and the plunger 16 with respect to the ambient atmosphere. It will be noted that the thread 32 may cooperate with the ears 18 and 18' so that, thanks to an effort of screwing represented by the arrow of rotation R in FIG. 3, the teeth 34 are firmly engaged in the band 14.

When the cap 30 is to be removed, it suffices to exert thereon an effort of rotation represented by arrow R' in FIGS. 3 and 4, this effort having the effect of displacing the cap 30 opposite the part 11 of the base 10, as represented by arrow $F_1$ in FIG. 4. As the flange 33 remains fast with the principal part 31*a* it must be extracted from the volume V, this being possible thanks to a radial expansion of the flange 23 and, more generally of the skirt 20, allowing the passage of the flange 33 of the cap 30 at the level of opening O. Such expansion is represented by arrows $F_2$ in FIG. 4.

The cooperation of the thread 32 and of the ears 18 and 18' allows the effort of rotation R' to be considerably increased in order to expand the flange 23 radially.

When the cap 30 has been removed, the nut 6 of the syringe 3 can be screwed on the sleeve 15, which induces a displacement of the plunger-needle 16 towards the internal volume of the flask 2. Such displacement allows the needle to pass through the stopper 5 in order to pour into the receptacle 2*a* liquid of which the flow is represented by arrow E in FIG. 5.

Figure 6:
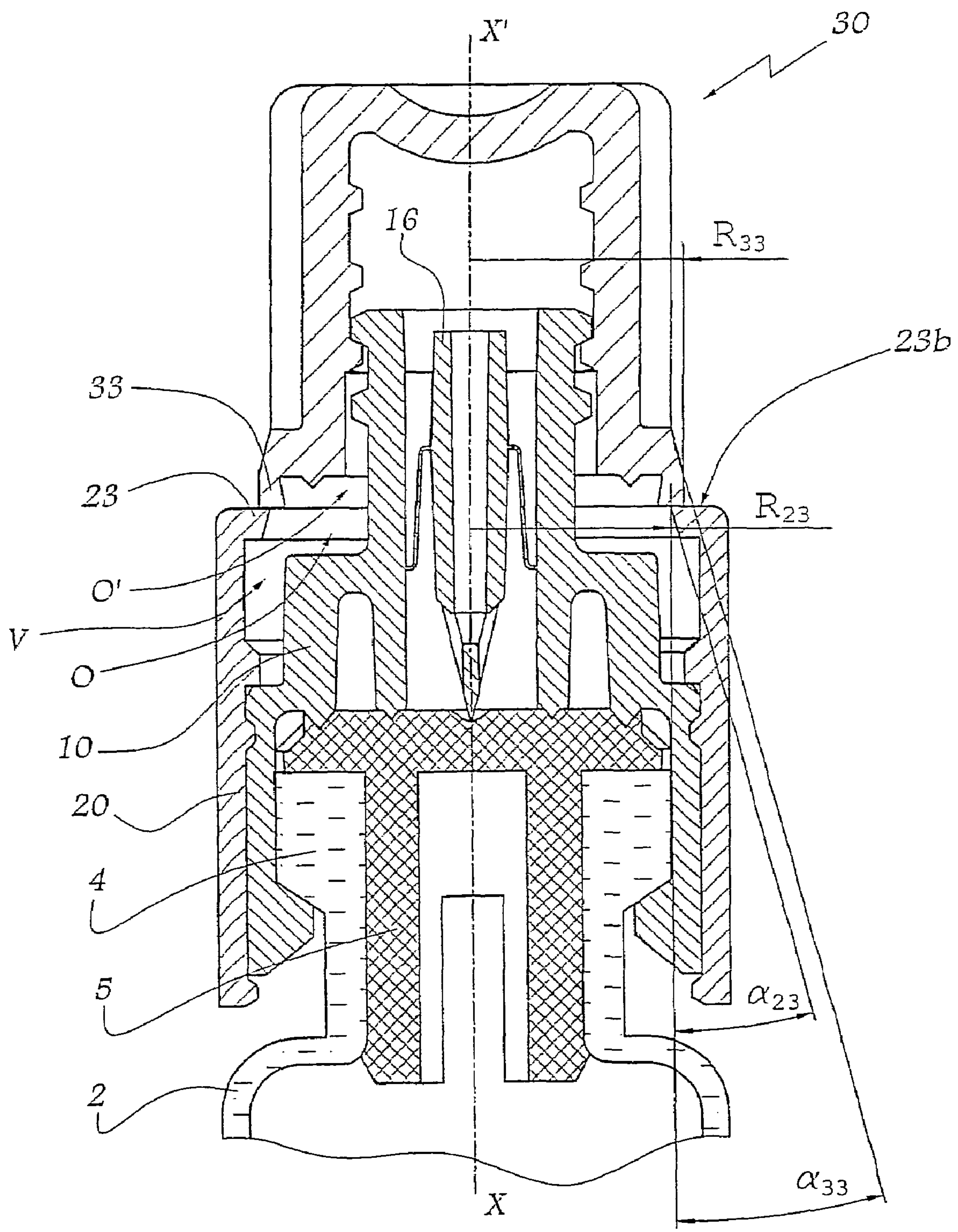
FIG. 6 is a section similar to FIG. 2 representing an attempt to replace the cap in position.

As shown in FIG. 6, if it is attempted to replace the cap 30 on the elements 10 and 20, the flange 33 opposes an introduction of the cap 30 through the opening O, the cap 30 in that case resting on the upper surface 23*b* of the flange 23, the total height of the device 1 in that case being different from that of this same device in the configuration of FIG. 3.

In other words, the respective values of the radii $R_{23}$ and $R_{33}$ are incompatible with an introduction of the cap 30 in the volume V through opening O.

Figure 7:
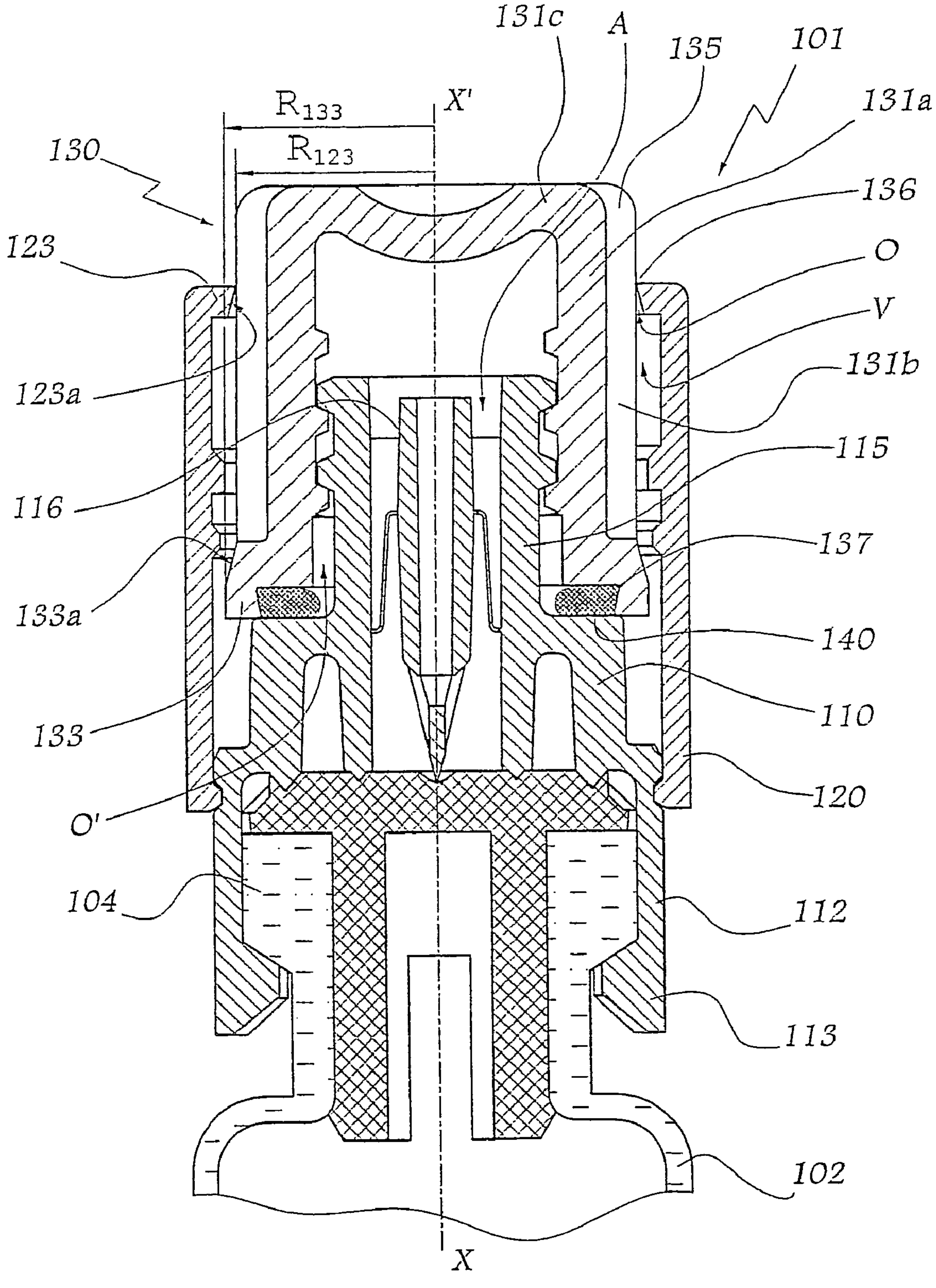
FIG. 7 is a section similar to FIG. 2 for a device according to a second form of embodiment of the invention.
Figure 8:
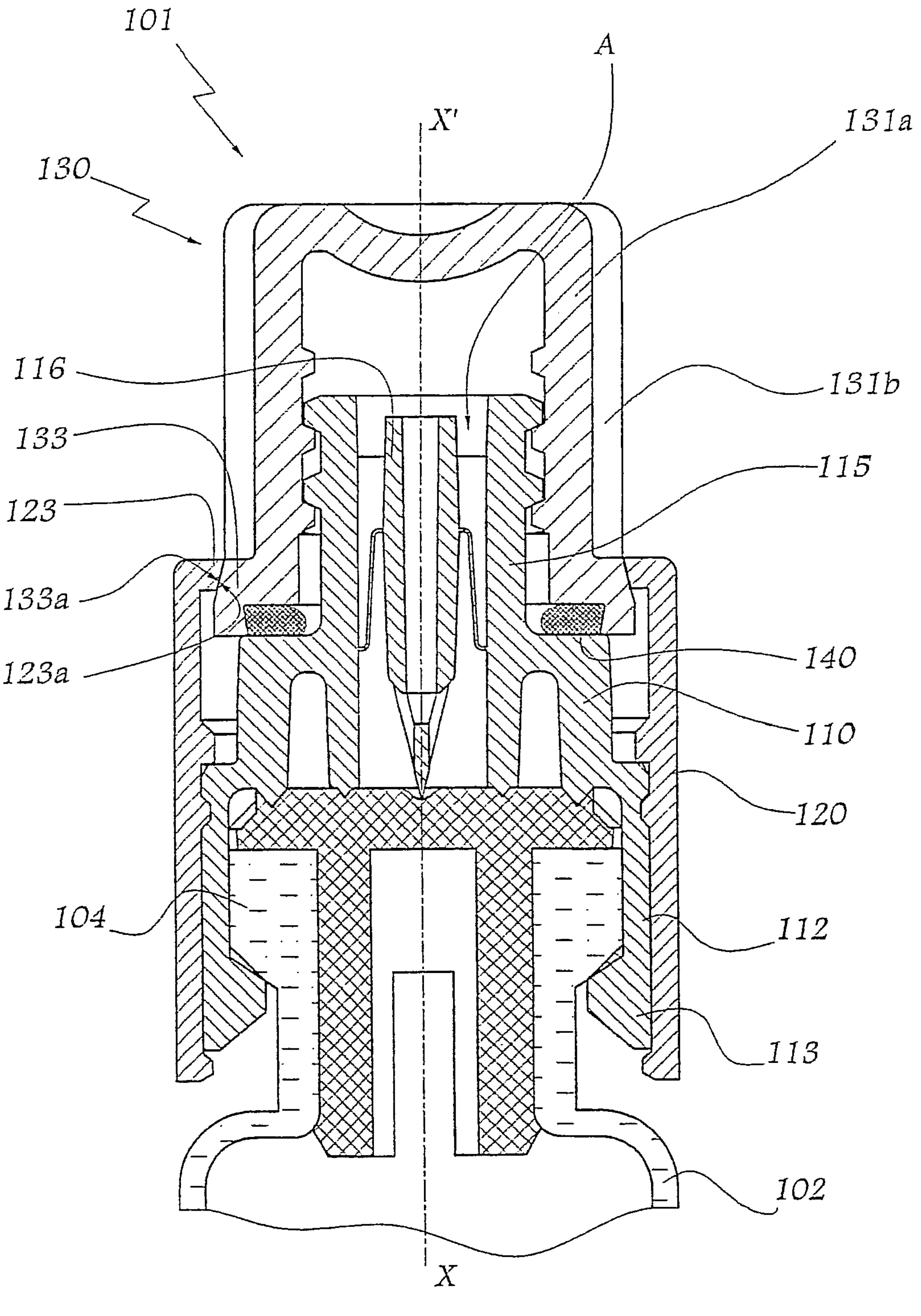
FIG. 8 is a section similar to FIG. 3 for the device of FIG. 7.
Figure 9:
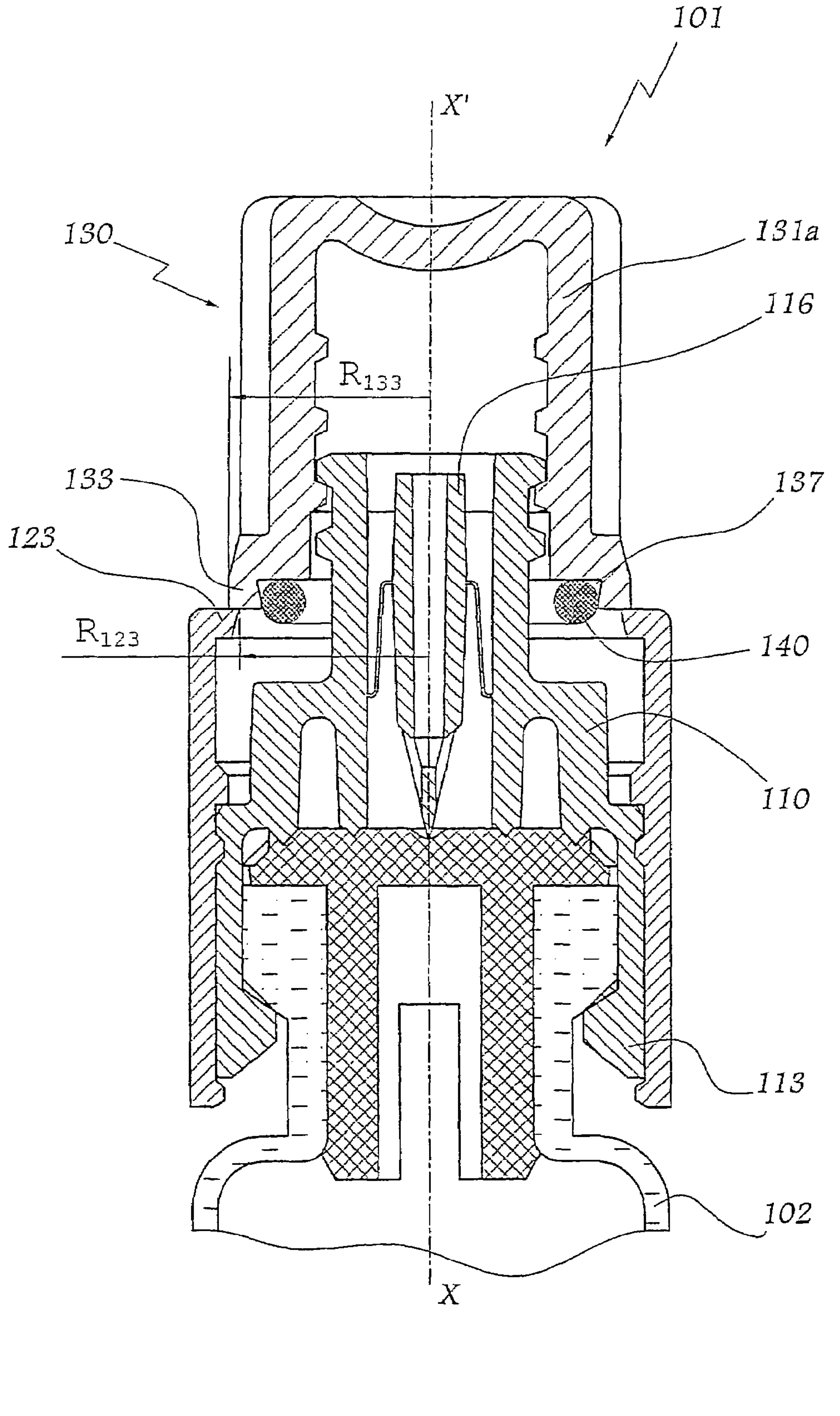
FIG. 9 is a section similar to FIG. 6 for the device of FIGS. 7 and 8.

In the second form of embodiment of the invention shown in FIGS. 7 to 9, elements similar to those of the first embodiment bear identical references increased by 100. The device 101 of this embodiment comprises a base 110 provided with tabs 112 presenting spouts 113 for fastening on the neck 104 of a flask 102. The base 110 forms a sleeve 115 which defines a bore A for slide of a plunger-needle 116. In practice, the base 110 is identical to the base 10 of the first embodiment.

A skirt 120 is provided to lock the tabs 112 around the neck 104, while a cap 130 is provided to isolate the base 110 from the ambient atmosphere. 131*a*, 131*b* and 131*c* respectively denote the principal part, the ribs for gripping and the bottom of the cap 130.

Elements 120 and 130 are made in one piece and joined, at the level of outer ribs 135 of the cap 130, by breakable bridges 136, the skirt 120 being able to pass from the configuration of FIG. 7 to that of FIG. 8 by rupture of these bridges 136.

As before, the skirt 120 is provided with a flange 123 defining an opening O providing access to the internal volume V of the skirt 120 and of which $R_{123}$ denotes the radius and 123*a* the inner radial face.

A flange 133 is provided in the vicinity of the opening O' of the cap 130 and 133*a* denotes its outer radial surface and $R_{133}$ its maximum radius.

As before, the radius $R_{133}$ is greater than radius $R_{123}$, this preventing a re-introduction of the cap 130 in the volume V through the opening O, from the configuration of FIG. 9.

An O-ring 140 made of Santoprene (Registered Trademark) is interposed between the cap 130 and the base 110. In practice, this O-ring is driven in a groove 137 of the cap 130 and is adjacent the opening O' of this cap.

This Santoprene O-ring makes it possible efficiently to isolate the internal volume of the cap 130 with respect to the ambient atmosphere independently of the use of teeth such as teeth 34 of the first embodiment. This O-ring is particularly adapted to the case of the product contained in the flask 2 being a vaccine or containing a molecule in liquid form which must be subjected to a terminal sterilization in an autoclave, at a temperature of about 120° C. and for a duration of about twenty minutes. Pieces made of polyethylene or polypropylene, such as the cap or the base, prove to be slightly deformed by a step of terminal sterilization. In effect, the temperature rise necessary during such sterilization induces a relaxing of the internal tensions of the matter and a decrease in the effort of pressure generated at the level of protuberances, such as the teeth 34 of the first embodiment. The efficiency of these teeth can therefore not be guaranteed.

Furthermore, it is not possible to use compounds based on styrene for making the pieces 110 and 130, as such compounds are degraded during a sterilization step as mentioned above.

An elastomeric O-ring therefore performs the function of seal, while being compatible with a sterilization step under the conditions mentioned above. The use of an injectable elastomer such as Santoprene is particularly advantageous as this material is stable at the temperatures in question and its cost price is satisfactory.

According to an advantageous aspect of the invention (not shown), the plunger of the device according to the invention may be equipped with a valve for controlling the flow of a fluid from or towards the internal volume of the receptacle.

According to another aspect of the invention (not shown), the flange 33 or 133 of the cap may be replaced by one or more protuberances extending over only a part of the circumference of the opening O'. Similarly, the flange 23 or 123 may be interrupted on one or more parts of the circumference of the opening O.

The characteristics of the two forms of embodiment shown may, of course, be combined together.

The invention claimed is:

1. A device for connection between a closed receptacle and a container, the closed receptacle comprising a neck of which the opening is closed by a stopper, the connection device comprising:

a base adapted to be mounted on the receptacle, comprising a sleeve forming an inner bore and adapted to be snapped on the neck;

a plunger adapted to slide in the bore between a first position, disengaged with respect to the stopper and a second position, in which a hollow needle traverses the stopper;

an annular skirt for locking the base in snap-on configuration on the neck, and a removable cap adapted to isolate the sleeve from ambient atmosphere, wherein the cap cannot be reinserted into its original position once removed, wherein the plunger and the base are formed in one piece and connected by at least one elastic tongue adapted to be deformed.

2. The device of claim 1, further characterized in that the at least one tongue is adapted to be deformed in a direction parallel to a central axis of the bore, in order to accompany the movement of the plunger between the first and second positions.

3. The device of claim 1, wherein the annular skirt is adapted with a flange for holding the separate removable cap.

4. The device of claim 1, wherein the cap is adapted to be removed to allow the connection of the container, the cap being provided with at least one protuberance adapted to be engaged in an internal volume of the skirt.

5. The device of claim 1, wherein the cap is adapted to be removed to allow the connection of the container, the cap being provided with at least one protuberance adapted to be engaged in an internal volume of the skiff, the protuberance extending radially with respect to a central axis of the neck and the cap over a distance greater than the minimum distance between the axis and an edge of an opening providing access to the internal volume of the skirt.

6. The device of claim 5, further comprising an O-ring made of elastomer interposed between the cap and the base when the protuberance is engaged in the internal volume.

7. The device of claim 5, further comprising an O-ring made of elastomer interposed between the cap and the base when the protuberance is engaged in the internal volume, wherein the O-ring is made of an injectable elastomer.

8. The device of claim 1, wherein the cap is adapted to be removed to allow the connection of the container, the cap being provided with at least one protuberance adapted to be engaged in an internal volume of the skiff, the protuberance extending radially with respect to a central axis of the neck and the cap over a distance greater than the minimum distance between the axis and an edge of an opening providing access to the internal volume of the skiff, the protuberance being joined a cover paff of the cap, wherein the protuberance is a flange presenting a radius greater than the inner radius of the edge which is substantially circular, and in that the skiff is elastically deformable and compatible with the extraction of the protuberance from its inner volume after radial deformation of the edge, such that the protuberance remains integral with the cover paff of the cap when the cap is removed from the device.

9. The device of claim 8, wherein the geometry of the protuberance and the geometry of the edge allow the extraction of the protuberance with respect to the internal volume through the opening and in a direction parallel to the axis of slide of the plunger and prevent an introduction of the cap in the volume through the opening.

10. The device of claim 8, wherein the flange presents an outer radial surface which is truncated and convergent towards the boffom of the cap while the edge is truncated and convergent opposite for snapping the device on the neck.

11. The device of claim 1, wherein the cap is provided with a tapping adapted to cooperate with at least one protuberance formed on the outer surface of the sleeve for positioning the cap along an axis of slide of the plunger.

12. The device of claim 1, wherein the cap and the skirt are made in one piece, of plastics material, breakable bridges being provided in order to join the cap and the skirt.

13. A ready-to-use assembly comprising:

a closed receptacle containing a product, the receptacle including a neck closed by a stopper;

a connection device mounted on the receptacle, the connection device comprising;

a base mounted on the receptacle, comprising a sleeve forming an inner bore and adapted to be snapped on the neck;

a plunger adapted to slide in the bore between a first position, disengaged with respect to the stopper and a second position, in which a hollow needle traverses the stopper;

an annular skirt for locking the base in snap-on configuration on the neck, and a removable cap adapted to isolate the sleeve from ambient atmosphere, wherein the cap cannot be reinserted into its original position once removed, wherein the plunger and the base are formed in one piece and connected by at least one elastic tongue adapted to be deformed.

14. The ready-to-use assembly of claim 13, further characterized in that the at least one tongue is adapted to be deformed in a direction parallel to a central axis of the bore, in order to accompany the movement of the plunger between the first and second positions.

15. The ready-to-use assembly of claim 13, wherein the annular skirt is adapted with a flange for holding the separate removable cap.

16. The ready-to-use assembly of claim 13, wherein the cap is adapted to be removed to allow the connection of the container, the cap being provided with at least one protuberance adapted to be engaged in an internal volume of the skirt.

17. The ready-to-use assembly of claim 13, wherein the cap is adapted to be removed to allow the connection of the container, the cap being provided with at least one protuberance adapted to be engaged in an internal volume of the skirt, the protuberance extending radially with respect to a central axis of the neck and the cap over a distance greater than the minimum distance between the axis and an edge of an opening providing access to the internal volume of the skirt.

18. The ready-to-use assembly of claim 13, wherein the cap is adapted to be removed to allow the connection of the container, the cap being provided with at least one protuberance adapted to be engaged in an internal volume of the skirt, the protuberance extending radially with respect to a central axis of the neck and the cap over a distance greater than the minimum distance between the axis and an edge of an opening providing access to the internal volume of the skirt, the protuberance being joined to a cover part of the cap, wherein the protuberance is a flange presenting a radius greater than the inner radius of the edge which is substantially circular, and in that the skirt is elastically deformable and compatible with the extraction of the protuberance from its inner volume after radial deformation of the edge, such that the protuberance remains integral with the cover part of the cap when the cap is removed from the device.

19. The ready-to-use assembly of claim 13, wherein the cap is provided with a tapping adapted to cooperate with at least one protuberance formed on the outer surface of the sleeve for positioning the cap along an axis of slide of the plunger.

20. The ready-to-use assembly of claim 13, wherein the cap and the skirt are made in one piece, of plastics material, breakable bridges being provided in order to join the cap and the skirt.

* * * * *

UNITED STATES PATENT AND TRADEMARK OFFICE

CERTIFICATE OF CORRECTION

PATENT NO. : 7,628,779 B2

APPLICATION NO. : 10/504837
DATED : December 8, 2009
INVENTOR(S) : Antoine Aneas It is certified that error appears in the above-identified patent and that said Letters Patent is hereby corrected as shown below:

In the Claims:

In Claim 5, Line 25, Column 7 change "skiff" to --skirt--.

In Claim 8, Line 40, Column 7 change "skiff" to --skirt--.

In Claim 8, Line 44, Column 7 change "skiff" to --skirt--.

In Claim 8, Line 47, Column 7 change "skiff" to --skirt--.

In Claim 8, Line 51, Column 7 change "paff" to --part--.

Signed and Sealed this

Thirtieth Day of March, 2010

David J. Kappos

*Director of the United States Patent and Trademark Office*